(12) United States Patent
Raberg

(10) Patent No.: US 10,458,813 B2
(45) Date of Patent: Oct. 29, 2019

(54) MAGNETIC FIELD SENSOR AND MAGNETIC FIELD SENSING METHOD

(71) Applicant: Infineon Technologies AG, Neubiberg (DE)

(72) Inventor: Wolfgang Raberg, Sauerlach (DE)

(73) Assignee: Infineon Technologies AG, Neubiberg (DE)

( * ) Notice: Subject to any disclaimer, the term of this patent is extended or adjusted under 35 U.S.C. 154(b) by 461 days.

(21) Appl. No.: 14/990,960

(22) Filed: Jan. 8, 2016

(65) Prior Publication Data

US 2016/0202086 A1 Jul. 14, 2016

(30) Foreign Application Priority Data

Jan. 9, 2015 (DE) .................. 10 2015 100 226

(51) Int. Cl.
*H05C 3/00* (2006.01)
*G01D 5/16* (2006.01)
*G01R 33/09* (2006.01)

(52) U.S. Cl.
CPC ............. *G01D 5/16* (2013.01); *G01R 33/093* (2013.01); *G01R 33/096* (2013.01); *G01R 33/098* (2013.01)

(58) Field of Classification Search
USPC ............................... 324/207.21, 207.25, 252
See application file for complete search history.

(56) References Cited

U.S. PATENT DOCUMENTS

| 7,400,137 | B1* | 7/2008 | Meguro | B82Y 25/00 324/207.21 |
|---|---|---|---|---|
| 7,535,215 | B2 | 5/2009 | Forster | |
| 8,063,633 | B2* | 11/2011 | Raberg | B82Y 25/00 324/252 |
| 2003/0011364 | A1* | 1/2003 | Hosomi | B82Y 25/00 324/252 |
| 2005/0185346 | A1* | 8/2005 | Shoji | B82Y 25/00 360/324.1 |
| 2006/0132126 | A1* | 6/2006 | Braun | G01D 11/245 324/260 |
| 2008/0012558 | A1* | 1/2008 | Rossler | B82Y 25/00 324/252 |
| 2008/0191694 | A1* | 8/2008 | Barton | G01R 33/09 324/252 |

(Continued)

FOREIGN PATENT DOCUMENTS

WO 2007/020154 A1 2/2007

*Primary Examiner* — Vincent Q Nguyen
(74) *Attorney, Agent, or Firm* — Eschweiler & Potashnik, LLC

(57) ABSTRACT

A magnetic field sensor is disclosed that includes at least one magneto-resistive spin-valve sensor element configured to sense a first magnetic field component $H_1$, and at least one AMR sensor element configured to sense a second magnetic field component $H_2$ which is perpendicular to the first magnetic field component $H_1$. In one example the at least one magneto-resistive spin-valve sensor element is a tunnel magneto-resistive (TMR) or giant magneto-resistive (GMR) sensor, and in one example the AMR sensor element includes an antiferromagnetic layer coupled to a ferromagnetic layer generating a bias magnetization for the AMR sensor element.

20 Claims, 9 Drawing Sheets

(56) References Cited

U.S. PATENT DOCUMENTS

| | | | |
|---|---|---|---|
| 2011/0101964 A1* | 5/2011 | Ausserlechner | G01D 5/145 324/207.11 |
| 2012/0032671 A1 | 2/2012 | Zimmer | |
| 2013/0320972 A1* | 12/2013 | Loreit | G01R 33/093 324/252 |
| 2014/0308757 A1* | 10/2014 | Ju | B81B 3/0032 438/3 |
| 2015/0022192 A1* | 1/2015 | Ausserlechner | G01D 5/145 324/207.25 |
| 2015/0061658 A1* | 3/2015 | Zimmer | H04L 47/525 324/207.25 |
| 2015/0185297 A1* | 7/2015 | Zimmer | G01R 33/093 324/252 |
| 2017/0241187 A1 | 8/2017 | Takayanagi | |

* cited by examiner

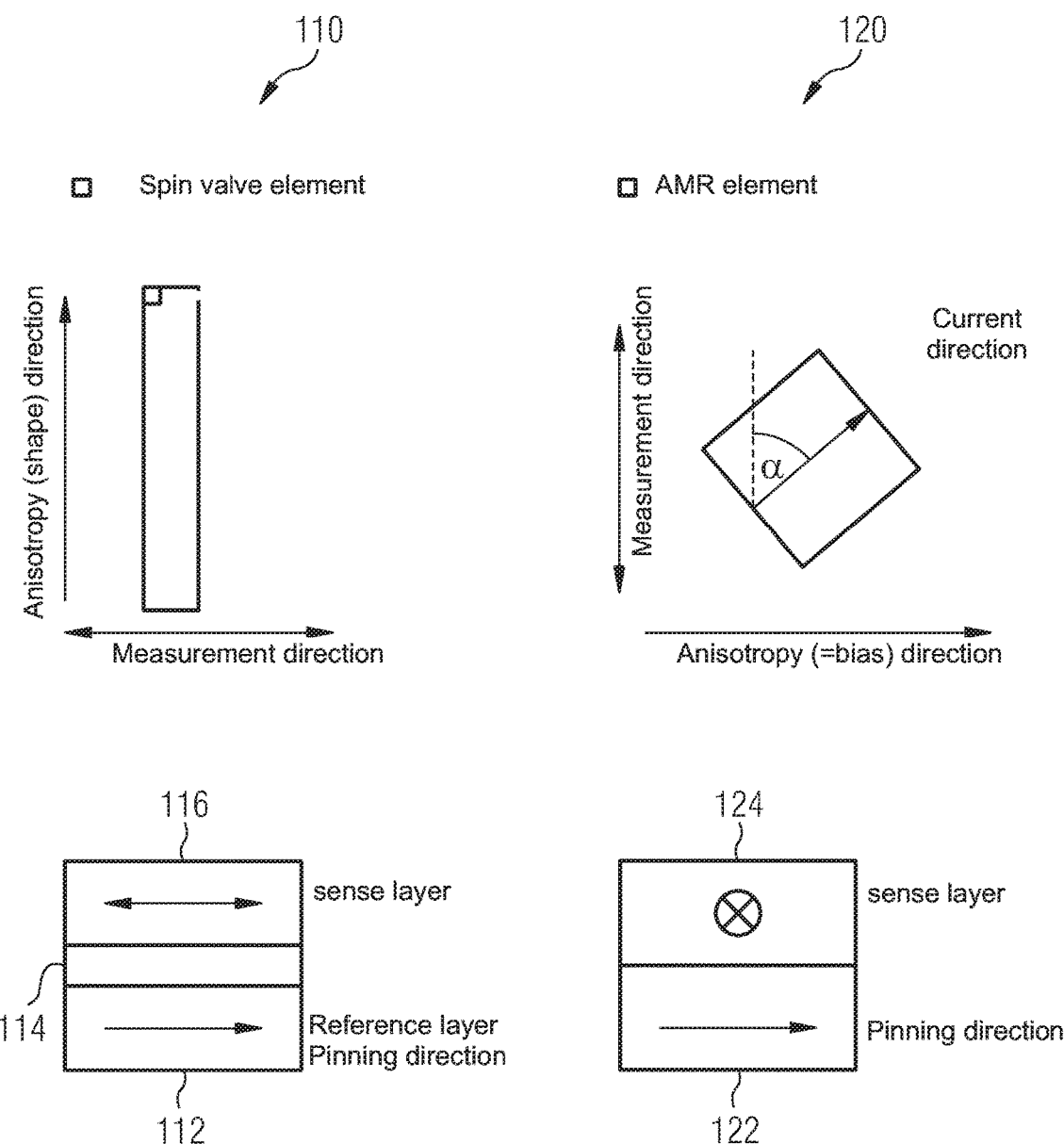

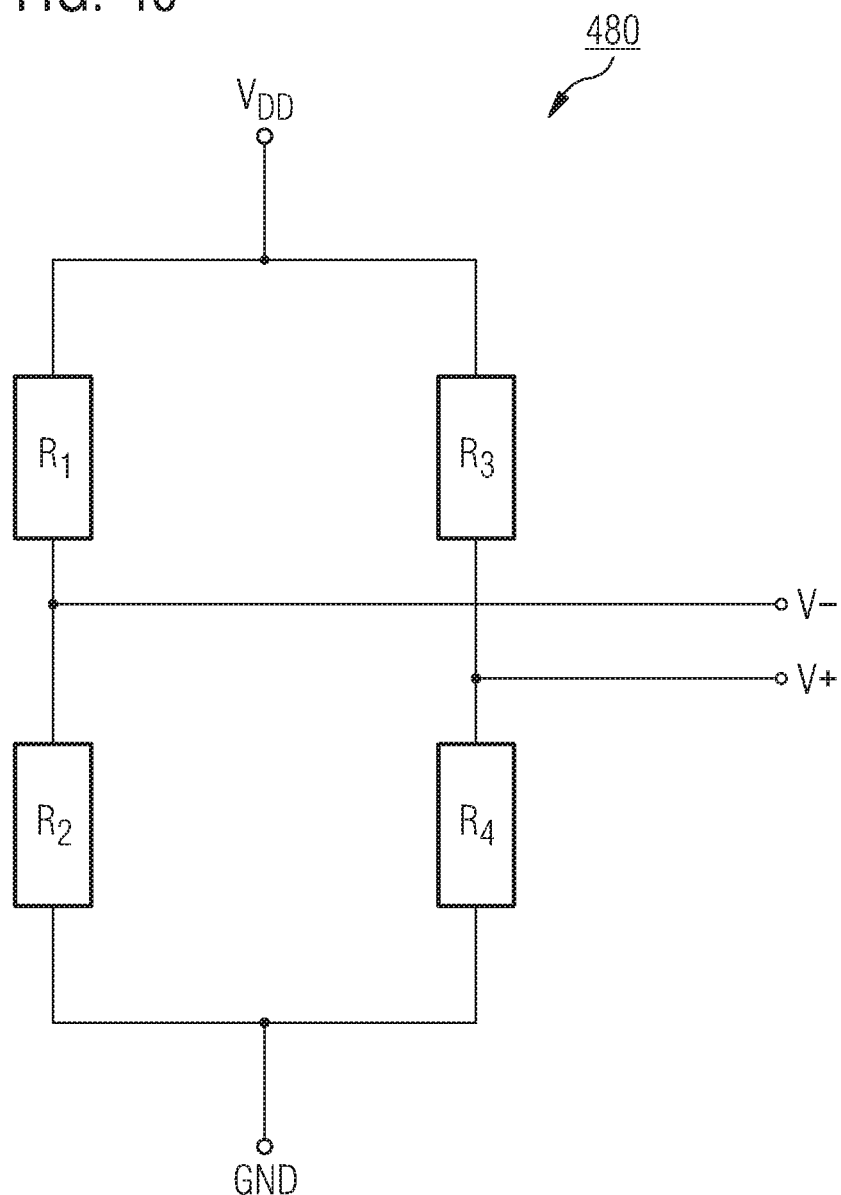

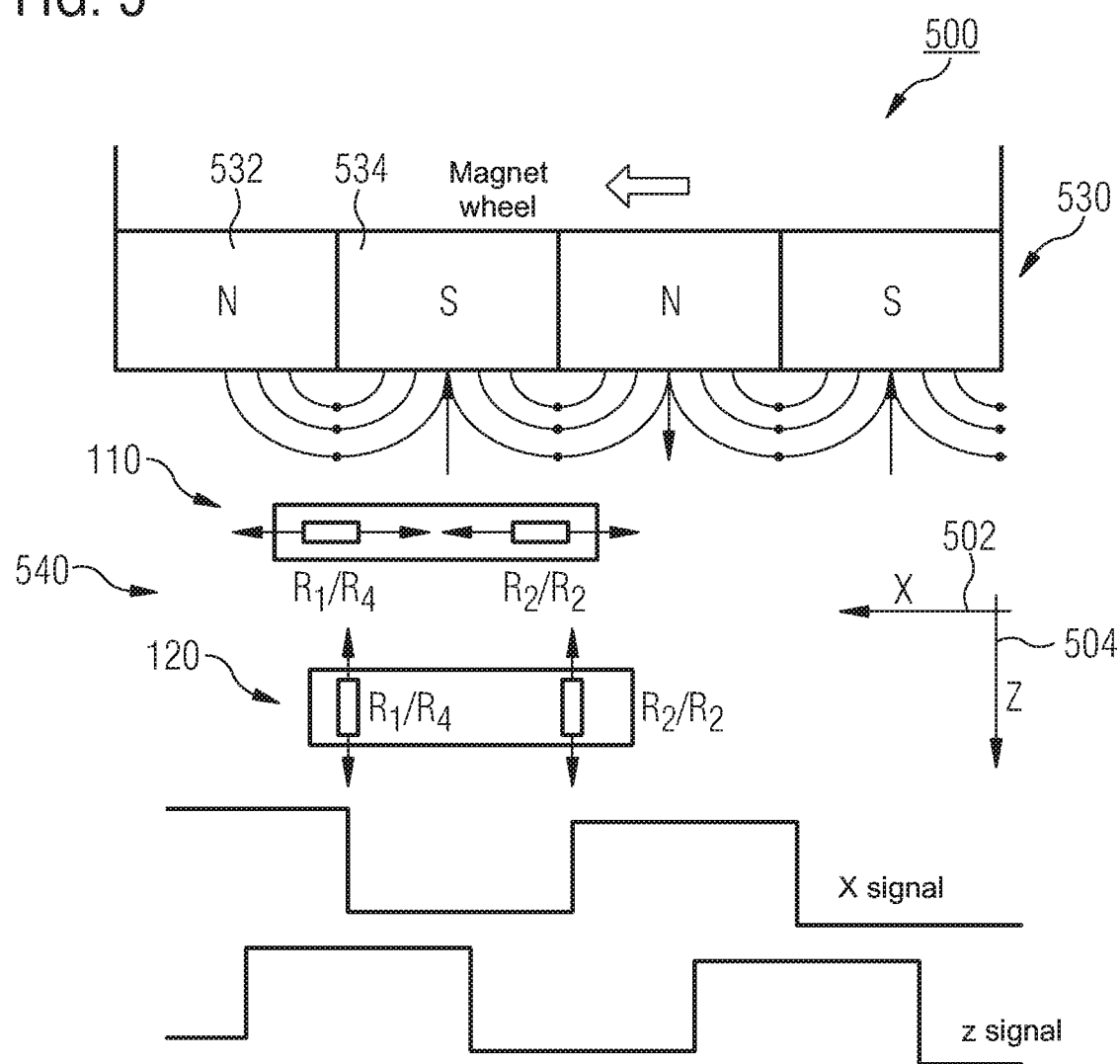

MAGNETIC FIELD SENSOR AND MAGNETIC FIELD SENSING METHOD

CROSS REFERENCE TO RELATED APPLICATION

This application claims priority to German Patent Application number 102 015 100 226.4 filed Jan. 9, 2015, which is hereby incorporated by reference in its entirety.

FIELD

Embodiments of the present disclosure generally relate to sensors and more particularly to magnetic field sensors.

BACKGROUND

In various applications there is a need for accurate, repeatable and reliable measurement of linear and/or rotary motion and position. For example, magnetic field sensors can be used for such linear and/or rotary motion and position sensing. For this purpose, for example, one or more permanent magnets may be attached to a magnetic encoder (target), and the magnetic field resulting from the encoder may be measured or sensed by one or more magnetic field sensors.

Some of today's magnetic field sensors make use of magneto-resistive sensors. Thereby, magneto-resistance denotes the property of a material or a multilayer device to change the value of its electrical resistance when an external magnetic field is applied to it. There are different materials and/or multilayer devices showing different types of magneto-resistance, including Anisotropic Magneto Resistance (AMR), Giant Magneto-Resistance (GMR), Colossal Magneto-Resistance (CMR), Tunnel Magneto-Resistance (TMR), or Extraordinary Magneto-Resistance (EMR). Magneto-resistive multilayer devices often come in a so-called spin-valve configuration comprising two or more conducting magnetic material layers, whose electrical resistance can change depending on the relative alignment of the magnetization in the layers.

New concepts for improved detection of the speed, position, or angles of a magnetic encoder call for robust magnetic field sensors capable of detecting simultaneously different magnetic field components generated or influenced by a magnetic encoder.

SUMMARY

Some simplifications may be made in the following summary, which is intended to highlight and introduce some aspects of the various example embodiments, but such simplifications are not intended to limit the scope of embodiments. Detailed descriptions of preferred example embodiments adequate to allow those of ordinary skill in the art to make and use the inventive concepts will follow in later sections.

According to a first aspect of the present disclosure, it is provided a magnetic field sensor. The magnetic field sensor includes at least one magneto-resistive spin-valve sensor element which is configured to sense a first magnetic field component. Further, it includes at least one Anisotropic Magneto-Resistive (AMR) sensor element which is configured to sense a second magnetic field component perpendicular to the first magnetic field component.

In some embodiments, the at least one magneto-resistive spin-valve sensor and the at least one AMR sensor element are integrated in a common sensor package.

In some embodiments, the at least one magneto-resistive spin-valve sensor element and the at least one AMR sensor element are formed on a common substrate.

In some embodiments, the at least one magneto-resistive spin-valve sensor element is a Tunnel Magneto-Resistive (TMR) or Giant Magneto-Resistive (GMR) sensor.

In some embodiments, the AMR sensor element comprises an antiferromagnetic layer coupled to a ferromagnetic layer to generate a bias magnetization for the AMR sensor element.

In some embodiments, a first exchange bias direction of the magneto-resistive spin-valve sensor element equals a second exchange bias direction of the AMR sensor element.

In some embodiments, the first and/or the second exchange bias direction is parallel or antiparallel to the first magnetic field component.

In some embodiments, the magnetic field sensor is further configured to route electrical current in an angle having an absolute value of 40°-50° with respect to the second exchange bias direction through the at least one AMR sensor element.

In some embodiments, the magnetic field sensor comprises a plurality of magneto-resistive spin-valve sensor elements forming at least a first Wheatstone bridge circuit, and a plurality of AMR sensor elements forming at least a second Wheatstone bridge circuit.

According to a further aspect of the present disclosure it is provided a magnetic sensor apparatus comprising a magnetic encoder configured to provide a magnetic field and also comprising a magnetic read sensor. The magnetic read sensor comprises at least one magneto-resistive spin-valve sensor element which is configured to sense a first component of the magnetic field and at least one AMR sensor element which is configured to sense a second component of the magnetic field perpendicular to the first component.

In some embodiments, the at least one AMR sensor element is positioned in a greater distance to the magnetic encoder than the at least one magneto-resistive spin-valve sensor element.

In some embodiments, the first component of the magnetic field is parallel to a direction of relative movement between the magnetic encoder and the magnetic read sensor.

In some embodiments, the second component of the magnetic field is parallel to a direction from a surface of the magnetic encoder towards the magnetic read sensor. The magnetic encoder's surface may face the magnetic read sensor.

In some embodiments, the magnetic encoder comprises a magnetic encoder wheel.

In some embodiments, the first component of the magnetic field corresponds to a tangential magnetic field component and the second component of the magnetic field corresponds to a radial or axial magnetic field component.

In some embodiments, the AMR sensor element comprises an antiferromagnetic layer coupled to a ferromagnetic layer in order to generate a bias direction in the at least one AMR sensor element.

In some embodiments, an exchange bias direction of the at least one magneto-resistive spin-valve sensor element corresponds to the exchange bias direction of the at least one AMR sensor element.

According to yet a further aspect of the present disclosure, it is provided a method for detecting a position and/or a speed of a magnetic encoder. The method includes using at least one magneto-resistive spin-valve sensor element to sense a first component of a magnetic field generated by the magnetic encoder, and using at least one AMR sensor element to sense a second component of the magnetic field perpendicular to the first component.

In some embodiments, the method further includes arranging the at least one magneto-resistive spin-valve sensor element and the at least one AMR sensor element on a common substrate.

In some embodiments, the method further includes providing a common exchange bias direction for the at least one magneto-resistive spin-valve sensor element and for the at least one AMR sensor element.

BRIEF DESCRIPTION OF THE DRAWINGS

Some embodiments of apparatuses and/or methods will be described in the following by way of example only, and with reference to the accompanying figures, in which FIG. 1 schematically illustrates a magnetic field sensor according to an embodiment;

FIG. 3 illustrates a schematic setup of a sensor including a magneto-resistive spin-valve sensor element and an AMR sensor element;

FIGS. 4a-4c show different implementations and examples of Wheatstone bridges;

FIG. 5 shows a magnetic sensor apparatus comprising a magnetic encoder and a magnetic read sensor, according to an embodiment;

DETAILED DESCRIPTION

Figure 1:
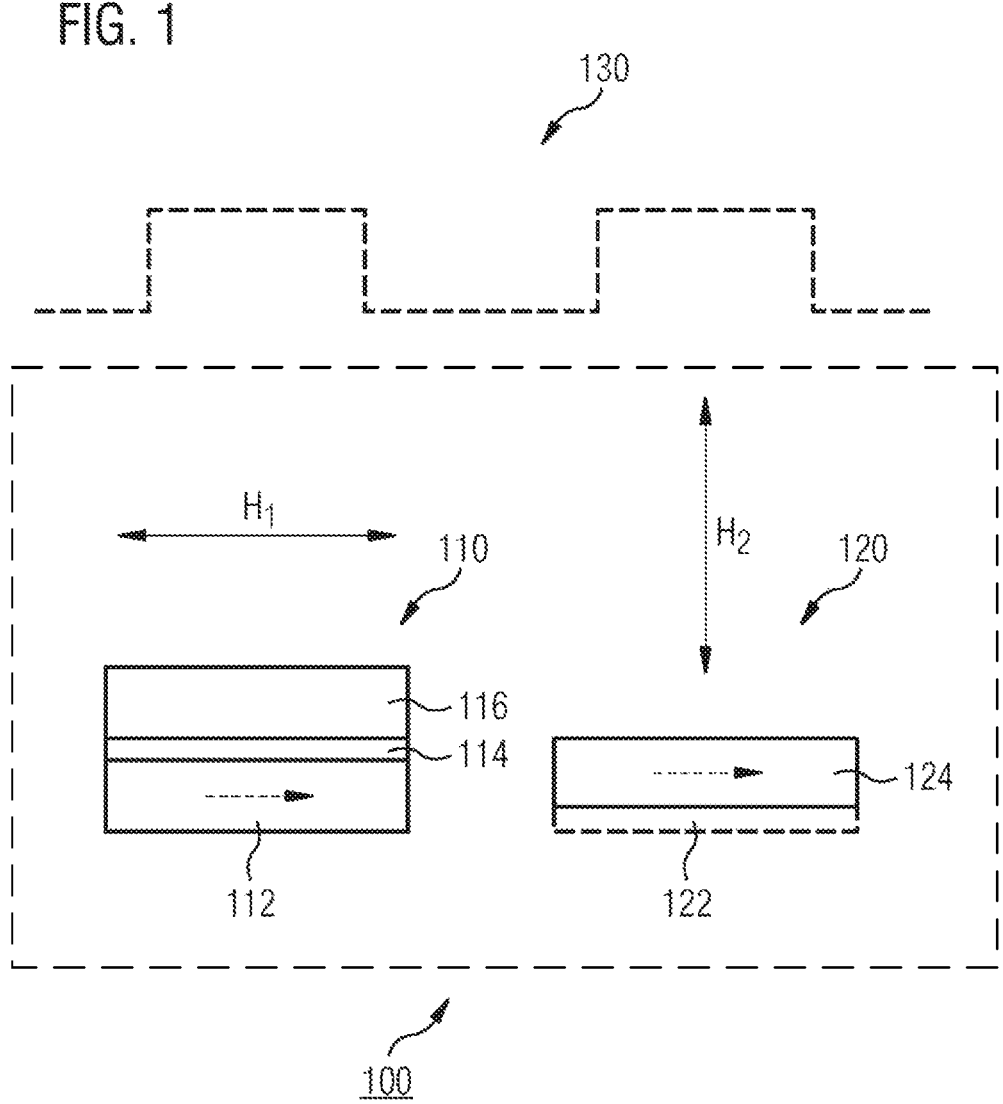

Various example embodiments will now be described more fully with reference to the accompanying drawings in which some example embodiments are illustrated.

Accordingly, while embodiments are capable of various modifications and alternative forms, embodiments are shown by way of example in the drawings and will herein be described in detail. It should be understood, however, that there is no intent to limit example embodiments to the particular forms disclosed, but on the contrary, embodiments are to cover all modifications, equivalents, and alternatives falling within the scope of the claims. Like numbers may refer to like elements throughout the description of the figures. It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or group thereof.

It should also be noted that in some alternative implementations, the functions/acts noted may occur out of the order noted in the figures. For example, figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art. However, should the present disclosure give a specific meaning to a term deviating from a meaning commonly understood by one of ordinary skill, this meaning is to be taken into account in the specific context this definition is given herein.

FIG. 1 schematically illustrates a magnetic field sensor 100 according to an example embodiment.

Magnetic field sensor 100 comprises at least one magneto-resistive spin-valve sensor element 110 which is configured to sense a first magnetic field component $H_1$. Further, magnetic field sensor 100 includes at least one Anisotropic Magneto-Resistive (AMR) sensor element 120 which is configured to sense a second magnetic field component $H_2$ perpendicular to the first magnetic field component. The magnetic field components $H_1$, $H_2$ may be generated or influenced by an optional magnetic encoder 130 generating or influencing an external magnetic field to be sensed.

Note that in three-dimensional space a magnetic field can be expressed by three mutually perpendicular field components. In a Cartesian (x, y, z) coordinate system, the first magnetic field component could be a component in x-direction, while the second magnetic field component could be a component in y- or z-direction. Similarly, based on rotary movements of a magnetic encoder 130, such as an encoder wheel, the first magnetic field component could be a component in tangential or circumferential direction, while the second magnetic field component could be a component in radial or axial direction, depending on the relative setup or locations of magnetic encoder 130 and sensor 100.

As illustrated in the example of FIG. 1, the spin-valve sensor element 110 may comprise a non-magnetic and/or isolating material layer 114 sandwiched between two ferromagnetic layers 112 and 116. Ferromagnetic layer 112 (e.g. NiFe, NiFeCo, etc.) may be fixed (pinned) by an antiferromagnet (not explicitly shown) which may act to shift a hysteresis curve. Some examples of antiferromagnetic materials are PtMn, NiMn, IrMn. The magnetic pinning is due to the so-called exchange bias or exchange anisotropy occurring in bilayers (or multilayers) of magnetic materials where the hard magnetization behavior of an antiferromagnetic thin layer causes a shift in the soft magnetization curve of a ferromagnetic layer. The ferromagnetic layer 112 and the antiferromagnetic layer may hence also be regarded as a reference system of the spin-valve sensor element 110. In contrast, the upper ferromagnetic layer 116 may be free (unpinned) and may behave as a "soft" layer. Due to the difference in coercivity, the soft layer 116 can change polarity at lower applied magnetic field strength than the pinned layer 112. Upon application of an external magnetic field (e.g., from magnetic encoder 130), the magnetization of soft layer 116 changes, resulting in an electrical resistance of spin-valve sensor element 110 dependent on the external magnetic field.

Note that the basic spin valve structure of FIG. 1 is mainly for illustrative purposes. However, the person skilled in the art will appreciate that other conventional multilayer spin valve structures may be used in order to implement an appropriate spin-valve configuration of sensor element 110.

In some embodiments, the at least one magneto-resistive spin-valve sensor element 110 may be implemented as a Giant Magneto-Resistive (GMR) sensor element. The GMR effect may be observed as a change in the electrical resistance of sensor element 110 depending on whether the magnetization of the adjacent ferromagnetic layers 112, 116 is in a parallel or an antiparallel alignment, for example. The overall resistance of sensor element 110 may be relatively low for parallel alignment and relatively high for antiparallel alignment. The magnetization of layer 116 can be influenced, for example, by applying an external magnetic field generated by the optional magnetic encoder 130, which is indicated by dotted lines in FIG. 1. The GMR effect is based on the dependence of electron scattering on the spin orientation. In case of a GMR sensor element, the thin non-magnetic spacer layer 114 may be electrically conductive (e.g. Cu, Cr, etc.).

In other embodiments, the at least one magneto-resistive spin-valve sensor element 110 may also be implemented as a Tunnel Magneto-Resistive (TMR) sensor element. The TMR effect is a magneto-resistive effect that occurs in a Magnetic Tunnel Junction (MTJ), which is a component comprising two ferromagnetic layers 112, 116 separated by a thin insulating layer 114 (tunnel barrier). If the electrically insulating layer 114 (e.g. MgO) is thin enough (typically a few nanometers), electrons may tunnel from one ferromagnetic layer into the other. The direction of the two magnetizations of the ferromagnetic layers 112, 116 can be switched individually by an external magnetic field. If the magnetizations are in parallel orientation it is more likely that electrons will tunnel through the insulating film than if they are in the antiparallel orientation. Consequently, such a junction can be switched between two states of electrical resistance, one with low and one with very high resistance.

Note that for GMR sensor elements as well as TMR sensor elements the illustrative layer 112 may be regarded as a bilayer of ferromagnetic layer fixed or pinned by an antiferromagnetic layer.

The AMR effect of sensor element 120 results from a property of a ferromagnetic material (e.g. Fe, FeNi, etc.) in which a dependence of electrical resistance on the angle between the direction of electric current and direction of magnetization is observed. Hence, in embodiments the AMR sensor element 120 may at least comprise a ferromagnetic layer 124.

In some embodiments, the at least one magneto-resistive spin-valve sensor element 110 and the at least one AMR sensor element 120 may be integrated in a common sensor package. In particular, the at least one magneto-resistive spin-valve sensor element 110 and the at least one AMR sensor element 120 may even be formed on a common substrate, e.g. a common semiconductor wafer. Depending on the application, the at least one magneto-resistive spin-valve sensor element 110 and the at least one AMR sensor element 120 may be formed adjacently on one side of the common substrate or on different sides (front and rear) of the common substrate.

Figure 2:
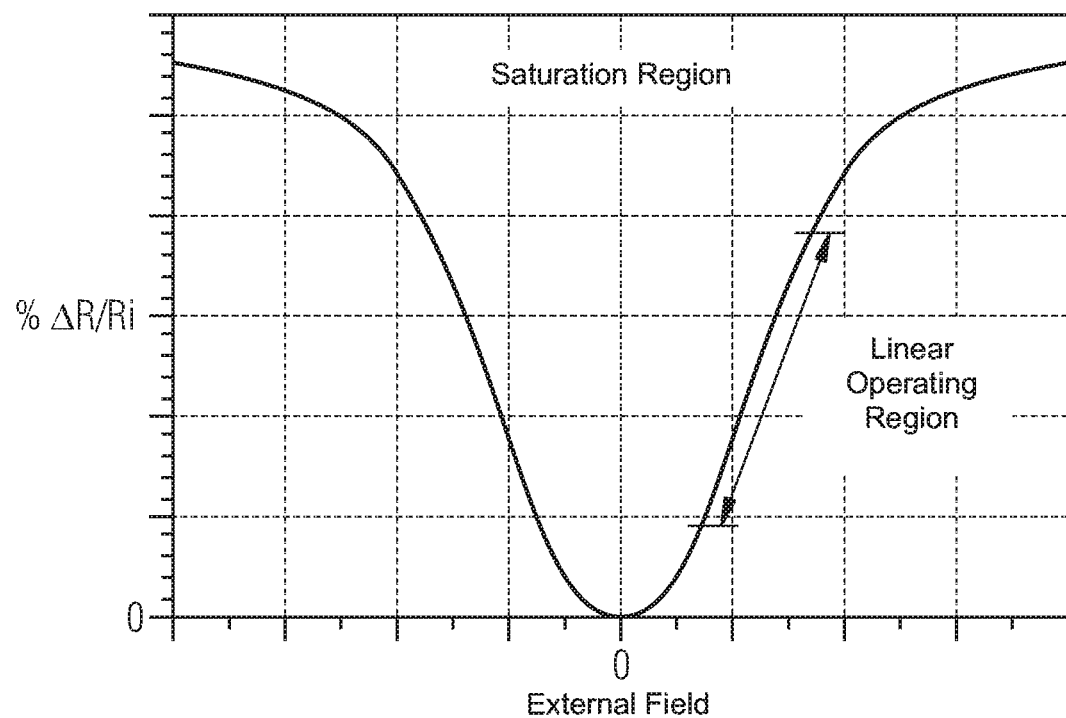
FIG. 2 illustrates some properties of the AMR effect.

FIG. 2 illustrates some properties of the AMR effect.

The magnetic response for an AMR sensor element can be expressed as the ratio of the change in resistance ($\Delta R$) over the nominal resistance (Ri) of the ferromagnetic layer 124. As can be seen from FIG. 2, the magnetic response is polarity insensitive, i.e., the response to a positive field is substantially the same as the response to a negative field. Notably, there is a region which is reasonably linear. However, the effect goes into saturation when the absolute value of the external magnetic field exceeds a particular value. Ferromagnetic materials, like Permalloy (FeNi), have magnetization, or magnetic moment per unit volume, which is a vector quantity defined at each point in the material. It is the rotation of this magnetization vector from the direction of the current flow due to an external magnetic field which produces the change in electrical resistance. For polarity sensitive applications, the ferromagnetic layer 124 of AMR sensor element 120 can be biased into the linear region of the curve by either rotating the magnetization away from the current, or by rotating the current away from the magnetization in the sensor design. In some embodiments, the AMR sensor element 120 may comprise an antiferromagnetic layer 122 coupled to the ferromagnetic layer 124 in order to generate such a bias magnetization for the AMR sensor element 120 via the exchange bias between antiferromagnetic layer 122 and ferromagnetic layer 124. Hence, the ferromagnetic layer 124 of AMR sensor element 120 can be biased into the linear region of the curve by an appropriate exchange bias direction.

In some embodiments, a first exchange bias direction of the magneto-resistive spin-valve sensor element 110 may equal a second exchange bias direction of the AMR sensor element 120. This option is indicated by the dashed arrows in the "pinned" ferromagnetic layers 112 and 124. In one embodiment, the antiferromagnetic layer 122 may even be shared between the magneto-resistive spin-valve sensor element 110 and the AMR sensor element 120. However, even if the pinned ferromagnetic layers 112 and 124 are separate from each other, at least the same exchange bias magnetization of both sensor elements 110, 120 may be set in a common process step by appropriate magnetic annealing, for example. The pinning of one of the respective ferromagnetic layers 112 and/or 124 may be achieved by annealing the respective layer in a magnetic field at a specified temperature. This annealing process may align the spin of the electrons in the respective pinned layers in one direction. In some embodiments, the first and/or the second exchange bias direction may be set parallel or antiparallel to the first magnetic field component $H_1$ to be sensed.

FIG. 3 illustrates a possible setup of the magneto-resistive spin-valve sensor element 110 and the AMR sensor element 120.

As can be seen from FIG. 3, the magneto-resistive spin-valve sensor element 110 may have considerably larger dimensions in the direction of the second magnetic field component $H_2$, i.e., in a direction perpendicular to its measurement direction which corresponds to the direction of the first magnetic field component $H_1$. Due to this shape anisotropy, the magneto-resistive spin-valve sensor element 110 may align its magnetic moment with its easy axis along the anisotropy direction, i.e., perpendicular to direction of the first magnetic field component $H_1$.

As can be seen from the right hand side of FIG. 3, the magnetic field sensor 100 may be configured to route electrical current through the at least one AMR sensor element 120 in an angle α having an absolute value of in a range from 40° to 50° with respect to its related measurement direction, i.e., with respect to direction of the second magnetic field component $H_2$. In one embodiment, the angle may have an absolute value of 45°, 135°, 225°, 315°, etc. Seen from another perspective, the magnetic field sensor 100 may be configured to route electrical current through the at least one AMR sensor element in an angle having an absolute value of 40°-50° (e.g., 45°) with respect to its related second exchange bias direction, which may be parallel or antiparallel to the direction of the first magnetic field component $H_1$.

Figure 4A:
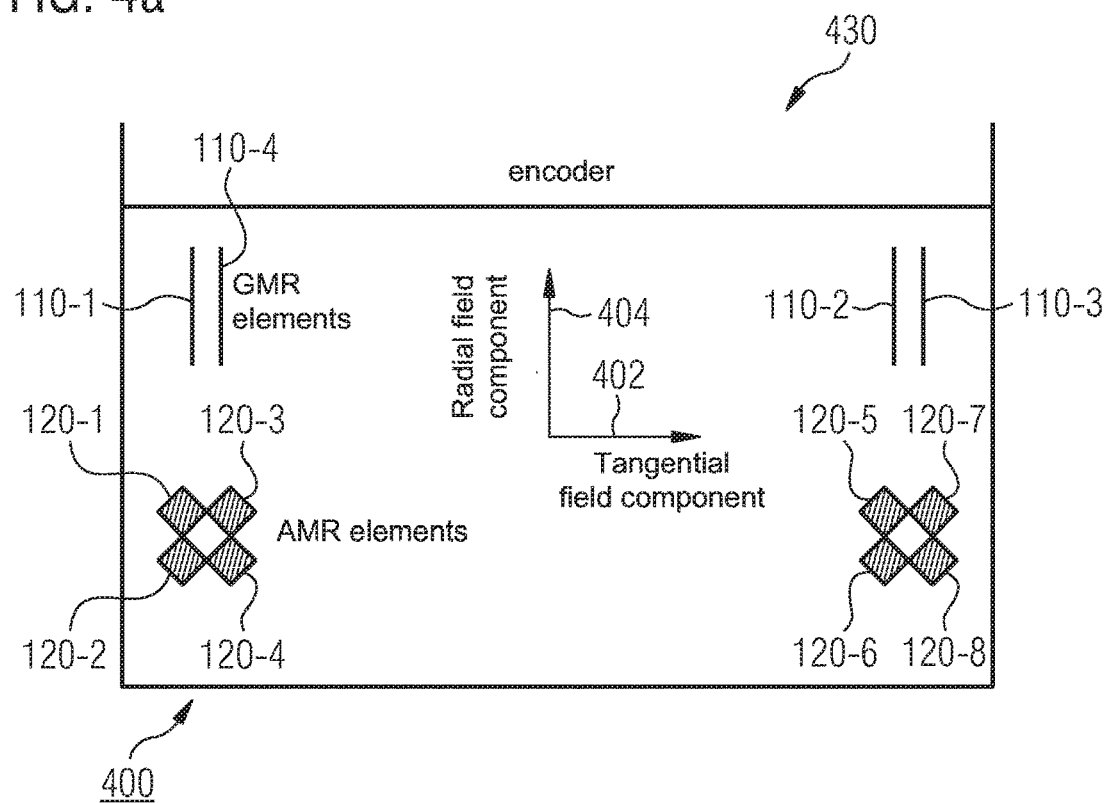
Figure 4B:
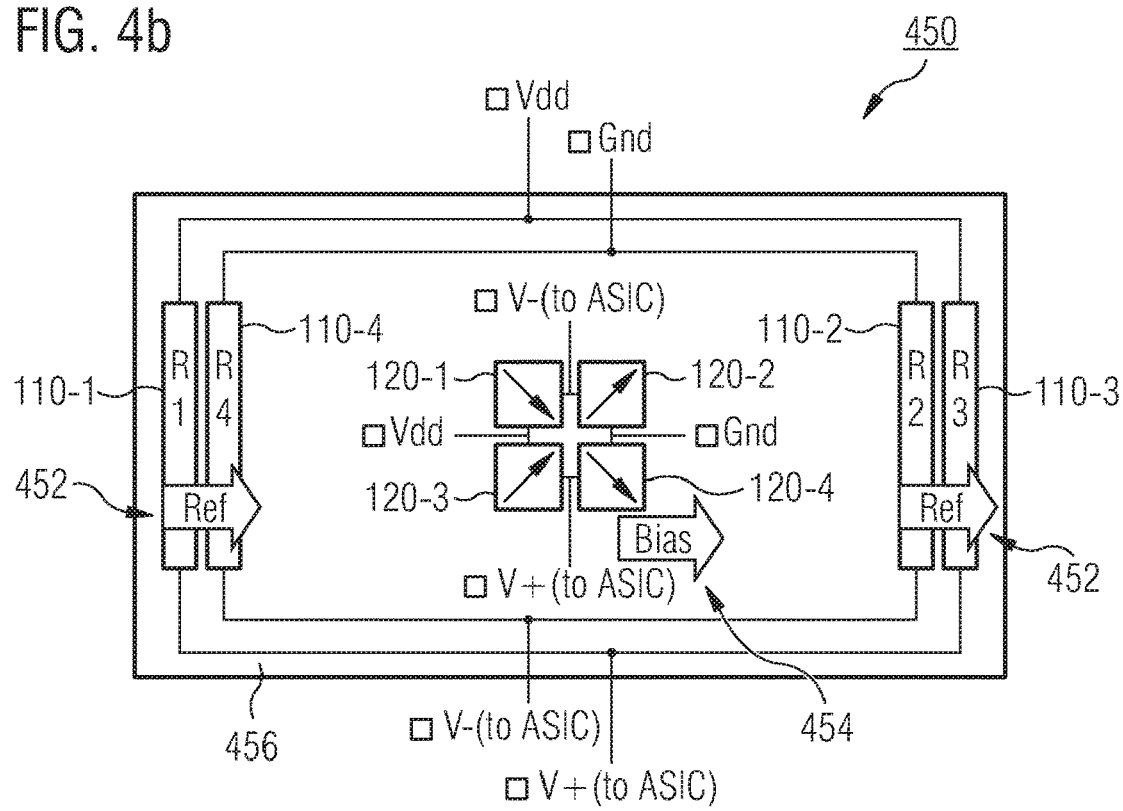

As can be seen from FIGS. 4a and 4b, example embodiments of the magnetic field sensor may comprise a plurality of magneto-resistive spin-valve sensor elements 110-1 to 110-4 forming at least a first Wheatstone bridge circuit, and a plurality of AMR sensor elements 120-1 to 120-4 (and optionally 120-5 to 120-8) forming at least a second Wheatstone bridge circuit. For higher signal amplitudes or better measurement results the magneto-resistive spin-valve sensor elements 110-1 to 110-4 and/or the AMR sensor elements 120-1 to 120-4 may be located at different positions with respect to a magnetic encoder. Note that functioning measurement bridge circuits may already be obtained by using only one magneto-resistive sensor element in the bridge circuit, respectively. However, applying more magneto-resistive sensor element may increase the sensitivity and/or accuracy of such bridge circuits.

An illustrative full Wheatstone bridge circuit 480 is shown in FIG. 4c.

The Wheatstone bridge circuit 480 comprises two parallel circuit branches coupled between supply voltage $V_{DD}$ and ground GND, for example. The first circuit branch includes a serial connection of two xMR elements $R_1$ and $R_2$, while the second circuit branch includes a serial connection of two xMR elements $R_3$ and $R_4$. Here, the expression "xMR" stands for the different magneto-resistive effects (e.g. AMR, GMR, TMR, etc.) discussed above. A differential measurement signal, e.g. a voltage, can be measured between a first terminal V− located between xMR elements $R_1$ and $R_2$ of the first circuit branch and a second terminal V+ located between xMR elements $R_3$ and $R_4$ of the parallel second circuit branch. The measurement signal is dependent on the changes of the xMR elements regarding their respective electrical resistance. The change of the respective electrical resistances in return is dependent on a currently prevailing external magnetic field at the respective xMR element's position.

Looking at the embodiment of FIG. 4b, it is illustrated an example implementation of a sensor circuit 450 comprising two Wheatstone bridges.

The magneto-resistive sensor circuit 450 comprises a first Wheatstone bridge circuit made from four magneto-resistive spin-valve sensor elements 110-1 to 110-4 and a second Wheatstone bridge circuit made from four AMR sensor elements 120-1 to 120-4. Here, two magneto-resistive spin-valve sensor elements 110-1 and 110-4 (corresponding to $R_1$ and $R_4$) are arranged at a left portion of sensor 450, while the other two magneto-resistive spin-valve sensor elements 110-2 and 110-3 (corresponding to $R_3$ and $R_4$) are arranged at an opposite right portion of sensor 450. This differential setup enables a measurement signal of rather large amplitude. Between the left magneto-resistive spin-valve sensor elements 110-1, 110-4 and the right magneto-resistive spin-valve sensor elements 110-2, 110-3 there is arranged the second Wheatstone bridge circuit comprising the AMR sensor elements 120-1 to 120-4. The AMR sensor elements 120-1 ($R_1$) to 120-4 ($R_4$) are coupled between supply voltage $V_{DD}$ and ground GND as has been explained with respect to FIG. 4c.

A first exchange bias direction 452 of the magneto-resistive spin-valve sensor elements 110-1 to 110-4 equals a second exchange bias direction 454 of the (multilayer) AMR sensor elements 120-1 to 120-4. In embodiments, the magneto-resistive spin-valve sensor elements 110-1 to 110-4 and the AMR sensor elements 120-1 to 120-4 may be arranged or formed on a common substrate 456, e.g. a common semiconductor wafer.

The example embodiment of FIG. 4a even comprises two AMR Wheatstone bridge circuits. While a first sensor part comprising the spatially differential Wheatstone bridge with magneto-resistive spin-valve sensor elements 110-1 to 110-4 may be sensitive to a tangential field component of a magnetic field generated by a magnetic encoder 430, a second sensor part comprising a spatially differential setup of two full Wheatstone bridges made of AMR sensor elements 120-1 to 120-4 and AMR sensor elements 120-5 to 120-8 may be sensitive to a radial (or axial) field component of the magnetic field generated by a magnetic encoder 430. The sensitivity of the magneto-resistive spin-valve sensor elements 110 may be adjusted by their respective exchange bias direction set along the tangential direction. Likewise, the sensitivity of the AMR sensor elements 120 may be adjusted by their respective in-stack exchange bias along the tangential direction 402. The measurement signal of each AMR Wheatstone bridge may be generated by appropriate current routing through the AMR resistors (e.g., at±45° w.r.t. to the radial field component 404).

In some embodiments, the tangential (i.e. first) component of the magnetic field may be parallel to a direction of relative movement between the magnetic encoder 430 and the magnetic sensor 400. The axial/radial (i.e. second) component of the magnetic field may be parallel to a direction from a surface of the magnetic encoder 430 facing the magnetic read sensor 400 towards the magnetic read sensor 400. In other words, if the tangential, axial, and radial directions span an x-, y-, z-coordinate system, the magneto-resistive spin-valve sensor elements 110-1 to 110-4 may be sensitive to magnetic field components in x-direction, while the AMR sensor elements 120-1 to 120-4 may be sensitive to magnetic field components in y- or z-direction.

FIG. 5 shows an example setup, where the magneto-resistive spin-valve sensor elements 110 are sensitive to magnetic field components in x-direction (e.g., the tangential direction), while the AMR sensor elements 120 are sensitive to magnetic field components in z-direction (e.g., the axial component).

The magnetic sensor system 500 of FIG. 5 includes a magnetic encoder 530 configured to provide a magnetic field to be sensed. Although the example magnetic encoder 530 of FIG. 5 comprises alternating permanent magnets 532, 534 of different magnetic polarity, other types of magnetic encoders are possible. For example, the encoders themselves not necessarily need to be magnetic as long as they are able to influence an external magnetic field. This is the case for ferromagnetic tooth wheels, for example, which are able to influence an external magnetic field generated by a nearby arranged permanent magnet. Also, the magnetic encoder 530 does not have to be a circularly extending encoder wheel as illustrated in the example of FIG. 5. Linearly extending multi-pole strips are also conceivable, for example.

Further, the example sensor system 500 comprises a respective magnetic sensor package 540 to sense the magnetic field. In the illustrated example embodiment, the magnetic sensor package 540 comprises a measurement bridge with at least one magneto-resistive spin-valve based sensor element 110 configured to sense a first component (x-component) 502 of the magnetic field, and a further measurement bridge with at least one AMR based sensor element 120 configured to sense a second component (z-component) 504 of the magnetic field perpendicular to the first component 502. The example of FIG. 5 illustrates respective measurement bridges comprising more than one respective sensor element.

A direction of relative movement between the encoder wheel 530 and the sensor package 540 may correspond to the x-direction, i.e., to the direction of the first magnetic field component 502. The second component (z-component) of the magnetic field may be parallel to a direction from a surface of the magnetic encoder 530, wherein the surface is facing the magnetic read sensor package 540, to the magnetic read sensor package 540. In the embodiment of FIG. 5 said surface corresponds to one end face of encoder wheel 530.

As can be seen from FIG. 5, the at least one AMR based sensor element 120 may be, in direction of the second magnetic flied component (z-component), located farther away from the magnetic encoder 530 than the at least one magneto-resistive spin-valve sensor element 110. In other words, the at least one AMR sensor element 120 may be positioned in a greater distance to a magnetic encoder 530 than the at least one magneto-resistive spin-valve sensor element 110 in order to avoid the magnetization of the AMR layer exceeding±45° with respect to the bias direction.

In the example configuration of FIG. 5, where the read sensor package 540 is located beside the magnetic encoder wheel 530 in axial direction, the direction of the second magnetic field component (z-component) corresponds to the axial direction. In an alternate top read configuration (not shown), where the sensor package 540 may be located radially outside the magnetic encoder wheel 530, the direction of the second magnetic field component (z-component) may corresponds to the radial direction. In both configurations, however, the direction of the first magnetic field component may correspond to the tangential direction 502.

Figure 6:
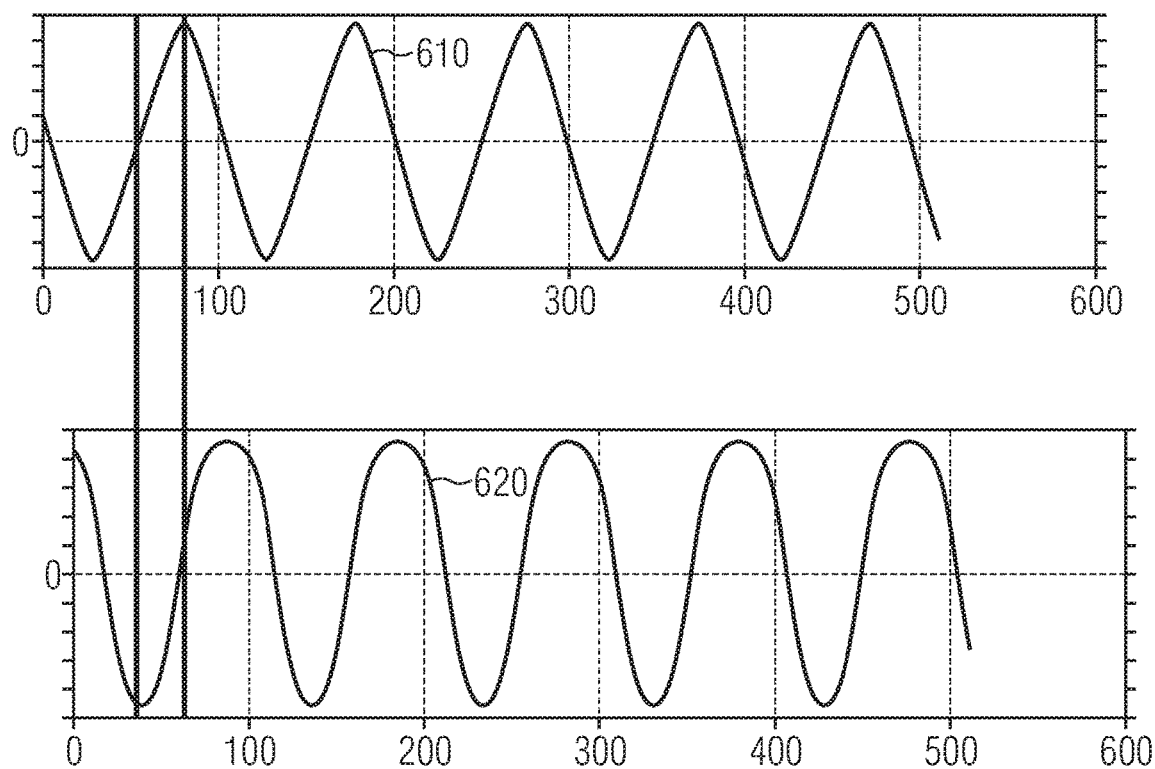
FIG. 6 illustrates exemplary measurement signals of an example magnetic field sensor system.

FIG. 6 illustrates exemplary measurement signals of the example magnetic field sensor system of FIG. 5.

The upper portion of FIG. 6 sketches a first periodic measurement signal 610 measured from the first measurement bridge comprising the at least one magneto-resistive spin-valve sensor element 110, while the lower portion of FIG. 6 shows a second periodic measurement signal 620 measured from the second measurement bridge comprising the at least one AMR sensor element 120. As can be seen from the signal courses, the measurement signals 610 and 620 are phase shifted by substantially 90°. As apparent from FIG. 5, the tangential field component (x-direction) is maximal at the boundary between S- and adjacent N-poles. Here, the axial or radial field component is minimal. Likewise, the axial/radial field component (z-direction) is maximal in the middle of an S- or N-pole. Here, the tangential field component is minimal.

An example process of manufacturing a magnetic field sensor package according to an embodiment is now described with respect to FIGS. 7a-7h.

Figure 7A:
FIGS. 7a-7h schematically illustrate a possible fabrication process of a magnetic field sensor according to an embodiment.

Firstly, as shown in FIG. 7a, a common substrate 702, e.g., a semiconductor wafer, including electrical wiring 704 for the different type sensor elements to be fabricated (spin-valve type and AMR-type) may be provided. This can be done via conventional semiconductor fabrication process steps.

Figure 7B:
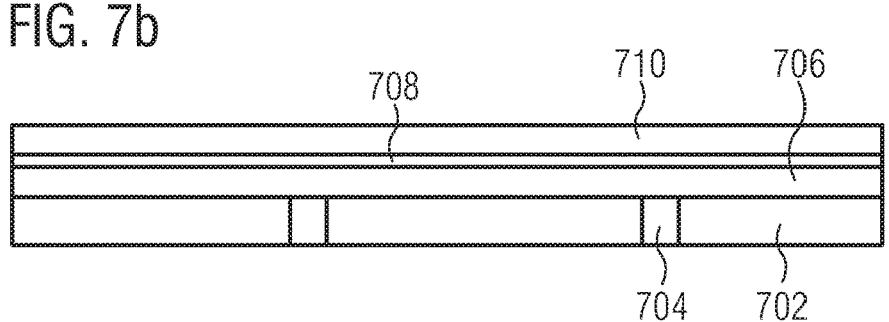

Further, as shown in FIG. 7b, a spin valve multilayer system may be deposited on the common substrate 702. Thereby, "deposition" may refer to any process that grows, coats, or otherwise transfers a material onto the wafer 702. Available technologies include Physical Vapor Deposition (PVD), Chemical Vapor Deposition (CVD), Electro-Chemical Deposition (ECD), molecular beam epitaxy (MBE), and Atomic Layer Deposition (ALD) among others. The spin valve multilayer system may include a reference layer system 706 (comprising e.g. antiferromagnetic and ferromagnetic layers), a spacer layer 708 (e.g. Cu), and a ferromagnetic sense layer 710 on top. Each layer may be deposited individually on top of the preceding layer.

Figure 7C:
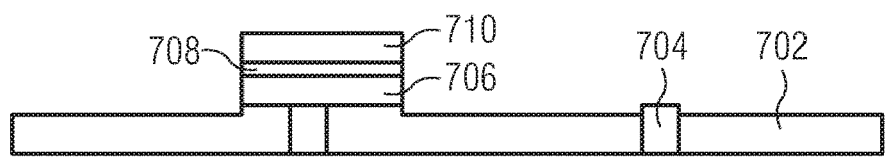

In a patterning act, shown in FIG. 7c, parts of the deposited spin valve multilayer system 706, 708, 710 are removed from the common substrate 702 by masking and etching the spin valve multilayers 706, 708, 710 to dimensions needed for one or more magneto-resistive spin-valve sensor elements 110. Here, conventional masking and etching means known from semiconductor production may be applied.

Figure 7D:
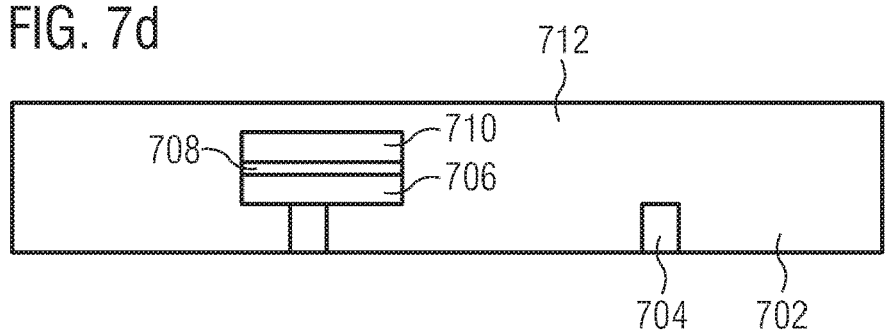

In a further act, shown in FIG. 7d, the remainder of the future magneto-resistive spin valve multilayer structure 706, 708, 710 is covered and surrounded by a protective insulating material 712, e.g. a dielectric material. Again, various deposition technologies may be applied.

Figure 7E:
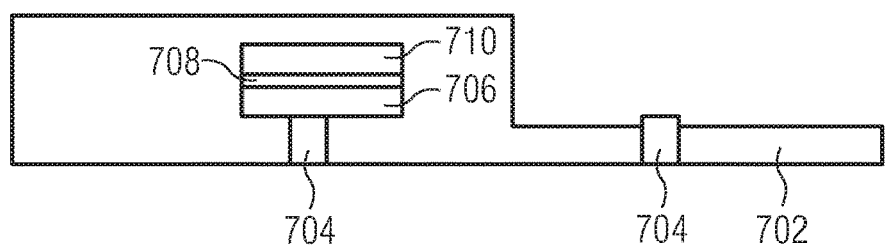

At the location(s) of the at least one (future) AMR sensor element, the protective isolating material 712 may be removed using conventional masking and etching means known from semiconductor production, see FIG. 7e.

Figure 7F:
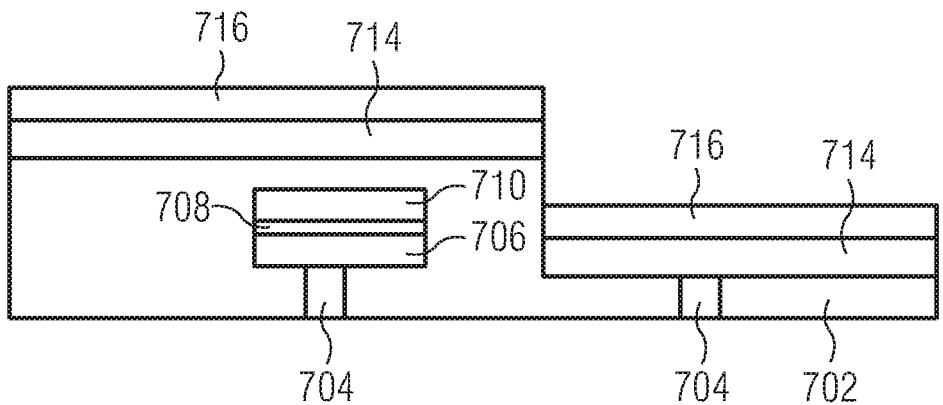

In a further act, shown in FIG. 7f, a system of a ferromagnetic layer 714 (sense layer) and an antiferromagnetic layer 716 may be deposited on top of the structure resulting from the previous process step of FIG. 7e. The ferromagnetic layer 714 may be a Permalloy (NiFe) layer, a NiFeCo layer, or a layer of other suitable materials known in the art. The material of the antiferromagnetic layer 716 may be PtMn, NiMn, IrMn, or similar.

Figure 7G:
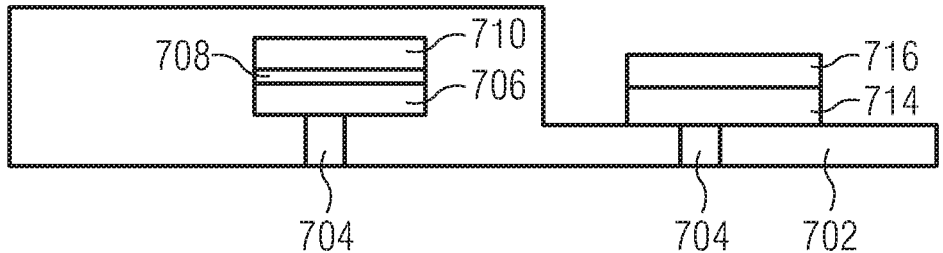

Again, as shown in FIG. 7g, parts of the deposited ferromagnetic layer 714 and antiferromagnetic layer 716 may be removed by masking and etching the layers 714, 716 to dimensions desired for one or more AMR sensor elements 120. Again, conventional masking and etching means known from semiconductor production may be applied for the patterning.

Figure 7H:
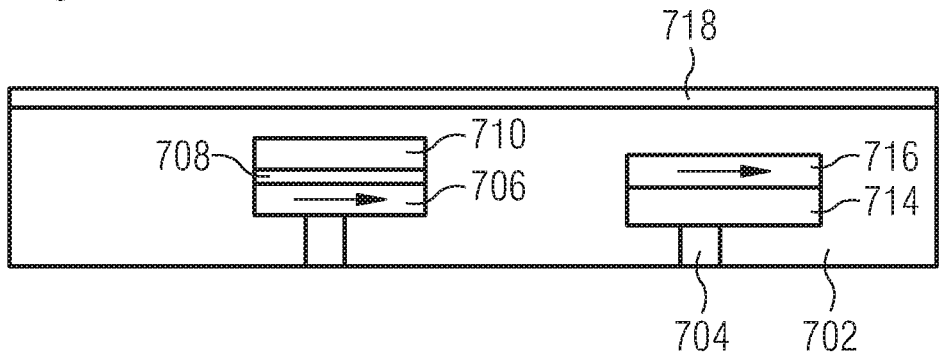

In further acts, illustrated in FIG. 7h, the remainder of the AMR bilayer structure 714, 716 may be covered and surrounded by protective insulating material 712, e.g. a dielectric material. The whole sensor arrangement may optionally be covered by a further protective layer 718. Further, an exchange bias direction common to both sensor elements 110 and 120 (indicated by the arrows in FIG. 7h) may be obtained by means of a common magnetic annealing process act. That is to say, a common exchange bias direction is provided for the reference system 706 (including a ferromagnetic layer) of the at least one magneto-resistive spin-valve sensor element 110 and for the ferromagnetic layer 712 of the at least one AMR sensor element 120. In some embodiments, the (antiferromagnetic and ferromagnetic) layers of reference system 706 of the at least one magneto-resistive spin-valve sensor element 110 and the layers (antiferromagnetic and ferromagnetic) 712, 714 of the at least one AMR sensor element 120 may even be obtained by the same process steps. In this way the production of the magnetic field sensor may be further improved.

Embodiments described in the present disclosure may provide improved detection of speed and position of a magnetic encoder (wheel). For that purpose the present disclosure proposes robust magnetic field sensors capable of simultaneously detecting the radial (or axial) components on the one hand and the tangential components on the other hand generated by the encoder. Embodiments can be used for cam- or crank sensor applications which require two sensor bridges with perpendicular sensitivity, respectively.

Some embodiments of the present disclosure propose to combine at least one spin-valve type TMR or GMR sensor for sensing the tangential field component with at least one AMR sensor with in-stack bias (generated by an exchange bias layer) for detecting the radial/axial field component. Besides providing a solution for the task at hand, an advantage of this combination may be that the exchange bias direction required for both sensors lies in the same direction, i.e., it can be set in the same process step. No local magnetization steps are required. The use of different sensing principles may also be helpful for ensuring functional safety of the sensor.

In a special embodiment, a first sensor for detection of the tangential field component may be formed as a spatially differential Wheatstone bridge made of GMR or TMR spin-valve elements with exchange bias direction set along the tangential direction. A second sensor for the detection of the radial/axial component may be formed as a spatially differential setup of two full Wheatstone bridges made of at least one AMR sensor with in stack exchange bias along the tangential direction. The signal within each Wheatstone bridge may be generated by appropriate current routing through the AMR resistors (at ±45° w.r.t. to the radial field).

An AMR device may for example be made as follows: a Permalloy layer may be deposited on a substrate in a first step. In a second step an antiferromagnetic material such as PtMn, NiMn, IrMn or similar may be deposited on top of the Permalloy layer. In a further step the sample is annealed in a magnetic field such that an exchange bias is formed in a direction perpendicular to the intended measurement direction. Subsequently, the layer stack is patterned and contacted to form e.g. a Wheatstone bridge with principally linear dependence on the magnetic field (e.g. by rotation of the current flow by 45° with respect to the measurement field direction or by using barberpole structures. Here, electrically conductive stripes of aluminum, gold, copper, tungsten or other suitable materials may be placed adjacently (e.g. below or above each other) to generate an effective current routing at around 45° with respect to the (exchange) bias direction.

In one embodiment the at least one AMR element may be further away from the magnetic encoder than the GMR element in order to avoid the magnetization of the AMR layer exceeding +−45° with respect to the bias direction.

The GMR and TMR spin-valve sensor elements can be formed as simple pinned, anti-parallel (AP) pinned or similar stacks in top spin valve or bottom spin valve geometry.

AMR can be formed as single ferromagnetic layers (eg NiFe, NiFeCo and other suitable materials) pinned by an antiferromagnet such as PtMn, NiMn, IrMn or similar. AMR elements can also be formed by using a coupling layer such as Ruthenium (Ru) between the sensing layer and the ferromagnetic layer coupled to the antiferromagnet.

The description and drawings merely illustrate the principles of embodiments of the invention. It will thus be appreciated that those skilled in the art will be able to devise various arrangements that, although not explicitly described or shown herein, embody the principles of example embodiments. Furthermore, all examples recited herein are principally intended expressly to be only for pedagogical purposes to aid the reader in understanding the principles of the invention and the concepts contributed by the inventor(s) to furthering the art, and are to be construed as being without limitation to such specifically recited examples and conditions. Moreover, all statements herein reciting principles, aspects, and embodiments of the invention, as well as specific examples thereof, are intended to encompass equivalents thereof.

It should be appreciated by those skilled in the art that any block diagrams herein represent conceptual views of illustrative hardware or circuitry embodying the principles of the invention. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Furthermore, the following claims are hereby incorporated into the Detailed Description, where each claim may stand on its own as a separate embodiment. While each claim may stand on its own as a separate embodiment, it is to be noted that—although a dependent claim may refer in the claims to a specific combination with one or more other claims—other embodiments may also include a combination of the dependent claim with the subject matter of each other dependent claim. Such combinations are proposed herein unless it is stated that a specific combination is not intended. Furthermore, it is intended to include also features of a claim to any other independent claim even if this claim is not directly made dependent to the independent claim.

Further, it is to be understood that the disclosure of multiple acts or functions disclosed in the specification or claims may not be construed as to be within the specific order. Therefore, the disclosure of multiple steps or functions will not limit these to a particular order unless such steps or functions are not interchangeable for technical reasons. Furthermore, in some embodiments a single step may include or may be broken into multiple sub steps. Such sub steps may be included and part of the disclosure of this single step unless explicitly excluded.

The invention claimed is:

1. A magnetic field sensor, comprising:
at least one magneto-resistive spin-valve sensor element configured to sense a first component of a magnetic field; and
at least one anisotropic magneto-resistive (AMR) sensor element configured to sense a second component of the magnetic field perpendicular to the first component of the magnetic field,
wherein the at least one magneto-resistive spin-valve sensor element and the at least one AMR sensor element have different structures, and
wherein the at least one magneto-resistive spin-valve sensor element and the at least one AMR sensor element are configured to simultaneously sense with one another.

2. The magnetic field sensor of claim 1, wherein the at least one magneto-resistive spin-valve sensor element is a tunnel magneto-resistive (TMR) or giant magneto-resistive (GMR) sensor.

3. The magnetic field sensor of claim 1, wherein the AMR sensor element comprises an antiferromagnetic layer coupled to a ferromagnetic layer generating a bias magnetization for the AMR sensor element via an exchange bias in a first exchange bias direction.

4. The magnetic field sensor of claim 3, wherein an exchange bias of the magneto-resistive spin-valve sensor element is in a second exchange bias direction equal to the first exchange bias direction of the AMR sensor element.

5. The magnetic field sensor of claim 4, wherein the first and/or the second exchange bias direction is parallel or antiparallel to the first component of the magnetic field.

6. The magnetic field sensor of claim 4, further configured to route electrical current in an angle having an absolute value of 40°-50° with respect to the first exchange bias direction through the at least one AMR sensor element.

7. The magnetic field sensor of claim 1, further comprising:
a plurality of magneto-resistive spin-valve sensor elements forming at least a first Wheatstone bridge circuit; and
a plurality of AMR sensor elements forming at least a second Wheatstone bridge circuit.

8. The magnetic field sensor of claim 1, wherein the at least one AMR sensor element is positioned a greater distance from a magnetic encoder than the at least one magneto-resistive spin-valve sensor element, wherein at least one AMR sensor element is spaced apart from the magnetic encoder by the at least one magneto-resistive spin-valve sensor element.

9. The magnetic field sensor of claim 1, wherein the at least one magneto-resistive spin-valve sensor element and the at least one AMR sensor element are formed on a common substrate.

10. The magnetic field sensor of claim 1, wherein the magnetic field is generated externally from the magnetic field sensor.

11. A magnetic sensor apparatus, comprising:
a magnetic encoder configured to provide a magnetic field; and
a magnetic read sensor, comprising:
at least one magneto-resistive spin-valve sensor element configured to sense a first component of the magnetic field; and
at least one anisotropic magneto-resistive (AMR) sensor element configured to sense a second component of the magnetic field perpendicular to the first component,
wherein the at least one magneto-resistive spin-valve sensor element has a different structure compared to the at least one AMR sensor element,
wherein the at least one magneto-resistive spin-valve element has larger dimensions in a direction of the second component relative to dimensions in a direction of the first component, and
wherein the at least one magneto-resistive spin-valve sensor element and the at least one AMR sensor element are configured to sense simultaneously with one another.

12. The apparatus of claim 11, wherein the first component of the magnetic field is parallel to a direction of relative movement between the magnetic encoder and the magnetic read sensor.

13. The apparatus of claim 12, wherein the second component of the magnetic field is parallel to a direction from a surface of the magnetic encoder facing the magnetic read sensor to the magnetic read sensor.

14. The apparatus of claim 11, wherein a first component of the magnetic field corresponds to a tangential magnetic field component and wherein a second component of the magnetic field corresponds to a radial or axial magnetic field component.

15. The apparatus of claim 11, wherein the AMR sensor element comprises an antiferromagnetic layer coupled to a ferromagnetic layer generating a bias direction in the at least one AMR sensor element.

16. The apparatus of claim 15, wherein an exchange bias direction of the at least one magneto-resistive spin-valve sensor element corresponds to the exchange bias direction of the at least one AMR sensor element.

17. A method for detecting a position and/or a speed of a magnetic encoder, the method comprising:
using at least one magneto-resistive spin-valve sensor element to sense a first component of a magnetic field generated by the magnetic encoder; and
using at least one anisotropic magneto-resistive (AMR) sensor element to sense a second component of the magnetic field perpendicular to the first component, wherein the at least one magneto-resistive spin-valve sensor element and the at least one AMR sensor element are used simultaneously, and wherein the at least one magneto-resistive spin-valve sensor element has a different structure than the at least one AMR sensor element.

18. The method of claim 17, further comprising:
arranging the at least one magneto-resistive spin-valve sensor element and the at least one AMR sensor element on a common substrate.

19. The method of claim 17, further comprising:
providing a common exchange bias direction for a ferromagnetic layer of the at least one magneto-resistive spin-valve sensor element and for a ferromagnetic layer of the at least one AMR sensor element.

20. The method of claim 17,
wherein the magnetic encoder is spaced from the at least one magneto-resistive spin-valve sensor element, and
wherein the at least one AMR sensor element is spaced from the at least one magneto-resistive spin-valve sensor element.

* * * * *